United States Patent
Hughes

(10) Patent No.: US 8,390,925 B2
(45) Date of Patent: Mar. 5, 2013

(54) LABORATORY SLIDE

(75) Inventor: Thomas Fergus Hughes, Eastbourne (GB)

(73) Assignee: Raymond A Lamb Limited, Eastbourne, East Sussex (GB)

( * ) Notice: Subject to any disclaimer, the term of this patent is extended or adjusted under 35 U.S.C. 154(b) by 103 days.

(21) Appl. No.: 12/158,604

(22) PCT Filed: Dec. 22, 2006

(86) PCT No.: PCT/GB2006/004928
§ 371 (c)(1),
(2), (4) Date: Aug. 28, 2008

(87) PCT Pub. No.: WO2007/072062
PCT Pub. Date: Jun. 28, 2007

(65) Prior Publication Data
US 2009/0225415 A1 Sep. 10, 2009

(30) Foreign Application Priority Data

Dec. 23, 2005 (GB) .................................. 0526452.8

(51) Int. Cl.
*B01L 3/00* (2006.01)
*G02B 21/34* (2006.01)
(52) U.S. Cl. ..................................... 359/396; 340/572.8
(58) Field of Classification Search ................... 359/396
See application file for complete search history.

(56) References Cited

U.S. PATENT DOCUMENTS

| | | | | |
|---|---|---|---|---|
| 5,561,556 A * | 10/1996 | Weissman | ...................... | 359/396 |
| 5,708,419 A * | 1/1998 | Isaacson et al. | ............ | 340/572.5 |
| 5,759,375 A * | 6/1998 | Stein et al. | ..................... | 204/616 |
| 6,024,285 A * | 2/2000 | Mish | ............................... | 235/492 |
| 6,634,560 B1 * | 10/2003 | Grabau | ......................... | 235/492 |
| 7,168,623 B1 * | 1/2007 | Royer | ............................ | 235/492 |
| 2002/0030598 A1 * | 3/2002 | Dombrowski et al. | .... | 340/572.1 |
| 2004/0241044 A1 | 12/2004 | Mordekhay | | |
| 2005/0051614 A1 * | 3/2005 | Albany | ......................... | 235/375 |
| 2006/0035247 A1 | 2/2006 | Ko | | |
| 2006/0153736 A1 * | 7/2006 | Kalra et al. | ...................... | 422/57 |
| 2007/0279735 A1 * | 12/2007 | Sieckmann | ................... | 359/396 |
| 2008/0213019 A1 * | 9/2008 | Walther et al. | ................. | 400/76 |
| 2010/0127067 A1 * | 5/2010 | Eisenberg et al. | ............ | 235/375 |

FOREIGN PATENT DOCUMENTS

DE    103 24 329 A1    12/2004
EP    1 048 723 A1    11/2000

(Continued)

OTHER PUBLICATIONS

Finkenzeller, Klaus, *RFID Handbook, Fundamentals and Applications in Contactless Smart Cards and Identification*, $2_{nd}$ Ed., John Wiley & Sons, 2003, Chapters 1, 2, and 12.

*Primary Examiner* — Mark Consilvio
(74) *Attorney, Agent, or Firm* — Fay Sharpe LLP

(57) ABSTRACT

A laboratory slide (2) for mounting, processing or storing a laboratory sample, has a recess (3) in a surface (4) of the slide (2). An inert sheet (5) has a chip (8) applied to the sheet (5) and the sheet (5) covers the recess (3) so that the chip (8) is fully received in the recess (3). The sheet (5) includes an antenna (6) which is arranged to establish communication between the chip (8) and an electric or electronic read/write device and the sheet (5) covers both the chip (8) and antenna (6) to protect them.

6 Claims, 1 Drawing Sheet

FOREIGN PATENT DOCUMENTS

| | | |
|---|---|---|
| GB | 2 379 739 A | 3/2003 |
| JP | 2004 125788 A | 4/2004 |
| JP | 2007309852 A * | 11/2007 |
| WO | WO 2005078648 A1 * | 8/2005 |
| WO | WO 2005/121865 A | 12/2005 |

* cited by examiner

LABORATORY SLIDE

This application is the national filing of and claims the benefit of PCT Patent Application Ser. No. PCT/GB2006/004928, filed on 22 Dec. 2006, and claims the benefit of Great Britain Patent Application No. 04526452.8.0, filed on 23 Dec. 2005, the disclosures of which are incorporated herein by reference.

The present invention relates to a laboratory slide for mounting processing and storing laboratory samples. More particularly, the invention is concerned with laboratory slides for storing information identifying the slides and the accompanying samples.

A laboratory slide can have a chip and an antenna enabling information to be stored on the slide and read. Such slides may be processed through many chemicals which could damage the chip and antenna.

DE-A-103 24 329 discloses a laboratory slide having a reusable, read writable programmable chip module and a gold plated electrical contact mechanical interface. The chip module is fixed to one side of the slide and the slide has a recess to locate the chip module on that side of the slide. A problem is that there is a risk of the chip module being damaged from chemicals during processing of the slide.

GB-A-2379739 discloses a laboratory slide for mounting, processing or storing a laboratory sample and has a micromodule applied to the surface of the slide. The micromodule has a memory medium for storing information and an antenna, which is printed on the slide surface, is used to connect the micromodule to an electric or electronic read/write device. The micromodule and antenna are overprinted with a protective ink which protects and conceals them and which forms a writing surface. A problem with this slide is that the micromodule, by projecting above the slide surface, may make it difficult for the protective ink properly to cover and, hence, adequately protect, the micromodule.

Also, if the laboratory slides described above are stacked there is a problem in that the stack is likely to be unstable.

It is an object of the present invention to alleviate the aforementioned problems.

The invention consists in a laboratory slide for mounting, processing or storing a laboratory sample, wherein a micromodule is disposed in a recess in a surface of the slide so that the micromodule is beneath or flush with said surface.

With the invention, the micromodule does not protrude above the slide surface and so enables such slides to be stacked in a stable manner. Also, the slide may have at least one inert sheet applied to it so as to cover the recess and micromodule. This provides protection for the micromodule from, for example, chemicals during processing of the slide. The sheet may be used as a writing or printing surface. The micromodule may be attached by being adhered, bonded or otherwise applied to the sheet prior to the application of the sheet to the slide and in a position so as to be disposed in the recess when the sheet is applied to the slide.

In order to transmit information between the micromodule and an electric or electronic read/write device, the slide may incorporate an antenna which is preferably disposed on a surface of the inert sheet. When an inert sheet is used it may cover and protect the antenna.

In one embodiment, the laboratory slide includes a slide extension which contains the recess for the micromodule. This slide extension is preferably of substantially the same thickness as the slide. The slide extension is preferably attached to the slide. The inert sheet may be attached to the slide and may be attached to the slide extension.

The micromodule has a memory medium for storing information. The micromodule may comprise a chip such as a radio frequency identification (RFID) chip, which operates in a contactless mode. The chip comprises an integrated circuit having a memory of the kind which is re-writable, such as an electrically erasable programmable read-only memory (EEPROM), so that information in the memory can be written over or erased by new information which is subsequently written to the memory using the electronic read/write device.

Embodiments of the present invention will now be described, by way of example, with reference to the accompany drawings, in which:—

Figure 1:
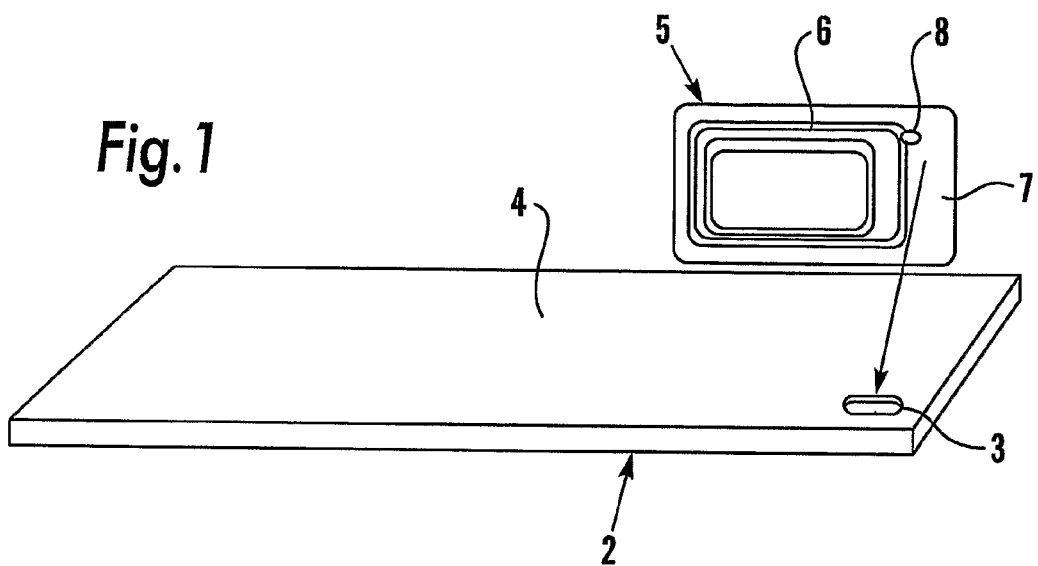
FIG. 1 is a schematic exploded perspective view of a laboratory slide according to one embodiment of the present invention.

Referring to FIG. 1 of the accompanying drawings, a laboratory slide is a glass slide 2 having an indent, recess or hollow 3 etched into a major surface 4 of the slide 2 and the indent 3 is positioned close to one corner of the slide 2.

A micro-thin inert plastic sheet 5 to be applied to the major surface 4 of the slide 2 and is as thin as possible to provide a minimal protrusion on the major surface 4. The sheet 5 has an antenna 6 printed on the underside 7 of the sheet 5. A micromodule 8 is applied to the sheet underside 7 using a surface mounting mechanism and is connected to the antenna 6. The micromodule 8 is in the form of an RFID chip which comprises an integrated circuit, and the antenna 6 serves as an interfacing means for electrically interfacing the integrated circuit to the circuit of a digital read/write device. The inert sheet 5 is applied to the glass slide 2 so that the chip 8 is received in the indent 3. The sheet 5 covers both the chip 8 and antenna 6 to protect them and supports the chip 8 within the indent 3. The inert sheet 5 may be bonded to the glass slide 2 using an epoxy resin.

Figure 2:
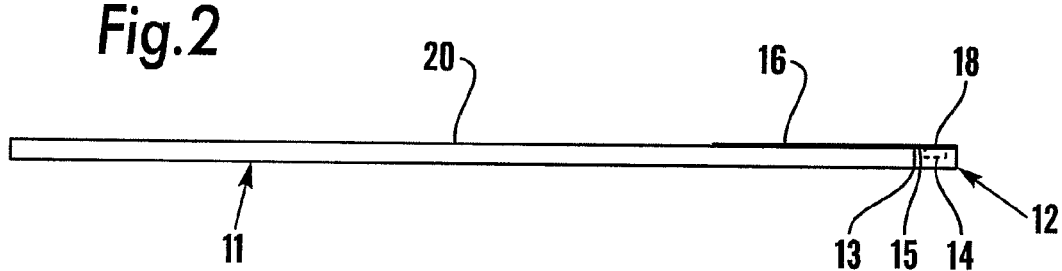
FIG. 2 is a schematic side view of a laboratory slide according to another embodiment of the present invention.
Figure 3:
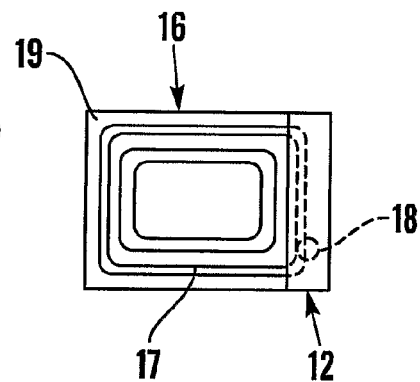
FIG. 3 is a view of the underside of a slide extension portion for the slide of FIG. 2.
Figure 4:
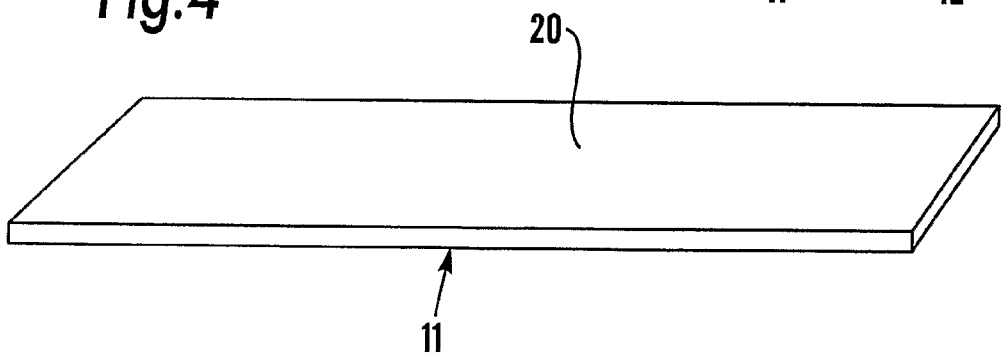
FIG. 4 is a perspective view of the main slide portion for the slide of FIG. 2.

Referring to FIGS. 2 to 4, a laboratory slide 11 is of glass and has an extension 12 of the same thickness projecting from one end 13. This slide extension 12 is in the form of a plastic strip and has an indent 14 in one surface 15.

Similarly to the embodiment described above, a micro-thin inert plastic sheet 16 has a printed antenna 17 and an RFID chip 18 on its underside 19, and the plastic slide extension 12 is bonded to the sheet underside 19 using a solvent resistant adhesive which may be ultra-violet (UV) cured. The slide extension 12 is attached to the sheet 16 so that the RFID chip 18 is contained within the indent 14 which is deep enough for the chip 18. The chip 18 is consequently flush with the slide extension surface 15 and the inert sheet 16 extends beyond one side of the slide extension 12. The slide extension 12 is bonded to the end 13 of the glass slide 11 using a solvent resistant adhesive which may be UV cured and the underside 19 of the sheet 16 may be bonded to a major surface 20 of the glass slide 11 using an epoxy resin. The bonded glass slide 11 and slide extension 12 form a rectangular shape with the slide extension surface 15 being coplanar with the major surface 20 of the glass slide 11.

Whilst particular embodiments have been described, it will be understood that various modifications may be made without departing from the scope of the invention. The micromodule 6 may comprise more than one integrated circuit and the glass slide 2 or slide extension 12 may have more than one indent. The antenna may be a copper antenna applied by an electroplating process.

The invention claimed is:

1. A combination of a laboratory slide and a separate slide extension for mounting, processing or storing a laboratory sample, the slide having an end, and the separate slide extension containing a recess extending inwardly from a surface of the slide extension, the slide extension being of substantially the same thickness as the slide, the slide extension being bonded to the end of the slide using a solvent resistant adhesive, the combination including;
   a micromodule for storing information identifying the slide, and dimensioned for receipt in the recess so that the micromodule is beneath or flush with the slide surface;
   an antenna for establishing communication between the micromodule and an associated electric or electronic read/write device; and
   at least one inert sheet formed of a material which provides a surface for writing or printing, the at least one inert sheet covering the recess and micromodule and sealing the micromodule in the recess, and the at least one inert sheet including the antenna received on one surface thereof which is on an opposite surface to the surface for writing or printing wherein the at least one inert sheet covers the antenna, and the one surface of the inert sheet having the micromodule applied thereto at a location that dimensionally aligns with the recess so the micromodule is positioned in the recess, the inert sheet having a reduced thickness to allow laboratory slides to be stacked one atop another, the at least one inert sheet extending over at least a portion of a surface of the slide and at least a portion of the surface of the slide extension.

2. The slide as claimed in claim 1, wherein the inert sheet is bonded to at least a portion of the surface of the slide and at least a portion of the surface of the slide extension.

3. The slide as claimed in claim 2, further comprising an epoxy resin for bonding the inert sheet to the at least a portion of the surface of the slide and to the at least a portion of the surface of the slide extension.

4. A method of constructing a laboratory slide having a slide extension for mounting, processing or storing a laboratory sample, including:
   providing a laboratory slide and a separate slide extension for mounting, processing or storing a laboratory sample, the slide having an end, and the separate slide extension, with a recess in a surface of the slide extension, a micromodule for storing information identifying the laboratory slide, and at least one inert sheet including an antenna for establishing communication between the micromodule and an electric or electronic read/write device;
   applying the micromodule to said at least one inert sheet;
   disposing the micromodule in the recess of the slide extension so that the micromodule is beneath or flush with said surface; and
   sealing the micromodule in the recess of the slide extension by covering the recess and micromodule with the at least one inert sheet, the at least one inert sheet providing a surface for writing or printing and an opposite surface which has the antenna wherein the at least one inert sheet covers the antenna, wherein the at least one inert sheet extends over at least a portion of a surface of the slide and at least a portion of the surface of the slide extension.

5. The constructing method of claim 4 further comprising making the slide extension to have substantially the same thickness as the slide.

6. The constructing method of claim 4 further comprising bonding the slide extension to the end of the slide.

* * * * *

UNITED STATES PATENT AND TRADEMARK OFFICE
CERTIFICATE OF CORRECTION

PATENT NO.      : 8,390,925 B2
APPLICATION NO. : 12/158604
DATED           : March 5, 2013
INVENTOR(S)     : Thomas Fergus Hughes It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 175 days.

Signed and Sealed this

First Day of September, 2015

Michelle K. Lee
*Director of the United States Patent and Trademark Office*